United States Patent [19]

Mathis et al.

[11] Patent Number: 5,599,341
[45] Date of Patent: Feb. 4, 1997

[54] LASER SURGICAL PROCEDURE AND DEVICE FOR TREATMENT OF THE CORNEA

[75] Inventors: Mark L. Mathis, Fremont; Thomas A. Silvestrini, Alamo, both of Calif.

[73] Assignee: Keravision, Inc., Fremont, Calif.

[21] Appl. No.: 259,886

[22] Filed: Jun. 15, 1994

[51] Int. Cl.$^6$ ................................................. A61B 17/36
[52] U.S. Cl. ........................................................... 606/5
[58] Field of Search ................................. 606/4, 5, 6, 10, 606/11

[56] References Cited

U.S. PATENT DOCUMENTS

| | | |
|---|---|---|
| 4,326,529 | 4/1982 | Doss et al. |
| 4,381,007 | 4/1983 | Doss. |
| 4,452,235 | 6/1984 | Reynolds. |
| 4,559,942 | 12/1985 | Eisenberg. |
| 4,671,276 | 6/1987 | Reynolds. |
| 4,688,570 | 8/1987 | Kramer et al. |
| 4,732,148 | 3/1988 | L'Esperance, Jr. ............... 606/4 |
| 4,766,895 | 8/1988 | Reynolds. |
| 4,815,463 | 3/1989 | Hanna. |
| 4,865,029 | 9/1989 | Pankratov et al. |
| 4,903,695 | 2/1990 | Warner et al. ..................... 606/4 |
| 4,941,093 | 7/1990 | Marshall et al. |
| 4,961,744 | 10/1990 | Kilmer et al. |
| 5,107,513 | 4/1992 | Sagie et al. |
| 5,112,328 | 5/1992 | Taboada et al. |
| 5,123,902 | 6/1992 | Müller et al. |
| 5,147,354 | 9/1992 | Boutacoff et al. |
| 5,196,027 | 3/1993 | Thompson et al. |
| 5,201,730 | 4/1993 | Easley et al. |
| 5,207,668 | 5/1993 | L'Esperance, Jr. |
| 5,219,343 | 6/1993 | L'Esperance, Jr. |
| 5,219,344 | 6/1993 | Yoder, Jr. |
| 5,222,952 | 6/1993 | Loertscher ......................... 606/6 |
| 5,242,438 | 9/1993 | Saadatmanesh et al. |
| 5,263,951 | 11/1993 | Spears et al. |
| 5,279,611 | 1/1992 | McDonnell et al. |
| 5,281,211 | 1/1994 | Parel et al. |
| 5,284,477 | 2/1994 | Hanna et al. |
| 5,364,390 | 11/1994 | Taboada et al. ................... 606/3 |
| 5,370,641 | 12/1994 | O'Donnell, Jr. .................... 606/6 |

OTHER PUBLICATIONS

Barraquer, "Basis of refractive keratoplasty–1967" *Refractive & Corneal Surgery* (1989) 5:179–193.

U.S. Patent and Trademark Office Official Gazette abstract of U.S. Pat. No. 5,314,422 to Nizzola (May 24, 1994), p. 2492.

Lexis™ printout of abstract and claims corresponding to U.S. Pat. No. 5,312,320 to L'Esperance, Jr., (May 17, 1994) (8 pages total).

Lexis™ printout of abstract and claims corresponding to U.S. Pat. No. 5,137,530 to Sand (Aug. 11, 1992) (1 page total).

Lexis™ printout of U.S. Pat. No. 5,304,167 to Freiberg (Apr. 19, 1994) (11 pages total).

Lexis™ printout of U.S. Pat. No. 5,147,354 to Boutacoff et al., (Sep. 15, 1992) (7 pages total).

Lexis™ printout of U.S. Pat. No. 5,037,421 to Boutacoff et al., (Aug. 6, 1991) (6 pages total).

*Primary Examiner*—Angela D. Sykes
*Assistant Examiner*—Sonja Harris-Ogugua
*Attorney, Agent, or Firm*—Morrison & Foerster

[57] ABSTRACT

This invention is a procedure and system for the correction of optical abnormalities in a hum, a eye. It involves the use of laser radiation to desiccate or ablate tissue in the stromal layer of the cornea. The procedure involved the initial step of forming at least one access site allowing access to the corneal volume behind Bowman's layer. The laser probe is then introduced into the access site and, depending upon the visual abnormality to be corrected, the probe is activated to adjust the volume of the corneal stromal layers. The shape of the volume desiccated or ablated is dependent upon the aberration to be corrected. In certain circumstances, radial or circumferential cuts in Bowman's layer may allow the curvature of the cornea to change following the corneal volume adjustment.

13 Claims, 6 Drawing Sheets

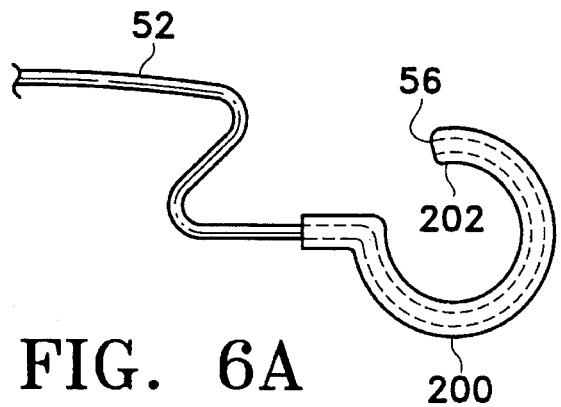
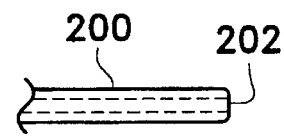
FIG. 6A  FIG. 6B
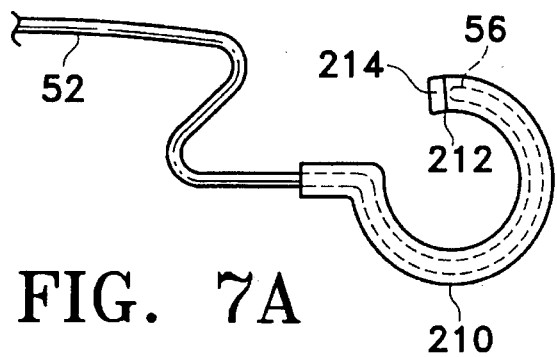
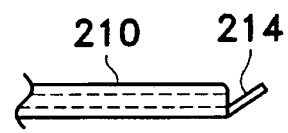
FIG. 7A  FIG. 7B
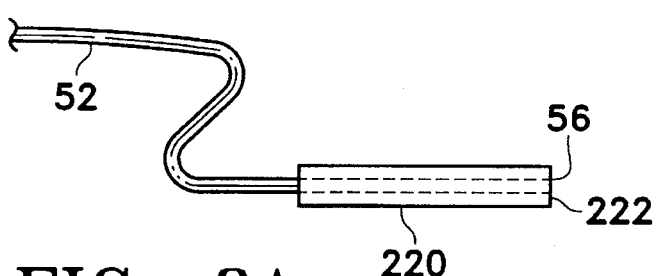
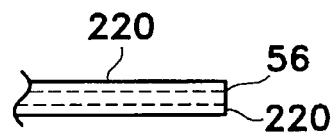
FIG. 8A  FIG. 8B
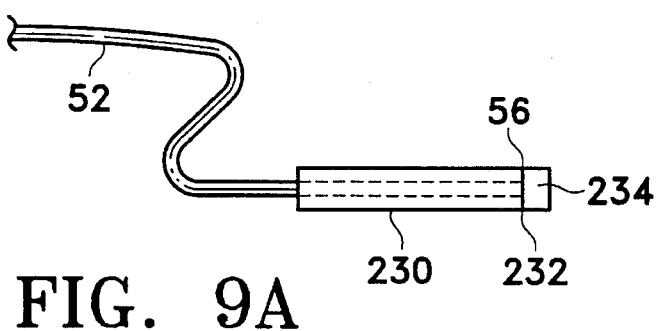
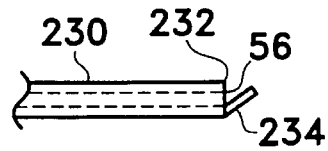
FIG. 9A  FIG. 9B

LASER SURGICAL PROCEDURE AND DEVICE FOR TREATMENT OF THE CORNEA

FIELD OF THE INVENTION

This invention is a procedure and device for the treatment of optical abnormalities in a human eye. It involves use of a device for directing laser radiation into the stomal body of the cornea. The procedure involves the initial step of forming at least one access site allowing access to the corneal volume behind Bowman's layer of the eye. The laser radiation is delivered through a fiber optic network to the access site. The type of laser for use in the procedure is selected dependent upon the visual abnormality to be corrected, whether the tissue is to be desiccated or ablated and the extent of desiccation or ablation required. For instance, if the optical aberration to be alleviated is hyperopia, a circular volume of tissue in the outer periphery of the cornea is removed. In other instances, such as for the treatment of astigmatism, certain smaller sections of the corneal volume may be shrunk. In certain circumstances, Bowman's layer may be cut to allow the curvature of the cornea to change after the corneal volume adjustment. These relief cuts may be radial, circular, semicircular or any other form appropriate for the optical adjustment desired.

BACKGROUND OF THE INVENTION

Anomalies in the overall shape of the eye can cause visual disorders. Hyperopia ("farsightedness") occurs when the front-to-back distance in the eyeball is too short. In such a case, parallel rays originating greater than 20 feet from the eye focus behind the retina. In contrast, when the front-to-back distance the eyeball is too long, myopia ("nearsightedness") occurs and the focus of parallel rays entering the eye occurs in front of the retina. Astigmatism is a condition which occurs when the parallel rays of light do not focus to a single point within the eye, but rather have a variable focus due to the fact that the cornea refracts light in a different meridian at different distances. Some degree of astigmatism is normal, but where it is pronounced, the astigmatism must be corrected.

Hyperopia, myopia, and astigmatism are usually corrected by glasses or contact lenses.

Another method for correcting those disorders is through the implantation of polymeric rings (intrastromal corneal rings or "ICR's") in the eye's corneal stroma to change the curvature of the cornea. Previous work involving the implantation of polymethylmethacrylate (PMMA) rings, allograft corneal tissue, and hydrogels is well documented. See, for instance, the use of PMMA intrastromal rings in U.S. Pat. Nos. 4,452,235 to Reynolds; 4,671,276 to Reynolds; 4,766,895 to Reynolds; and 4,961,744 to Kilmer. One of the ring devices described is a split ring that is inserted into a channel previously dissected in the stromal layer of the cornea. A minimally invasive incision is used both for producing the channel and for inserting the implant.

Both surgical and nonsurgical methods for reshaping the surface of the cornea have been developed. Radial keratotomy, described in U.S. Pat. Nos. 4,815,463 and 4,688,570, alters corneal curvature using radial incisions that extend through 80% to 95% of the cornea. Nonsurgical reshaping of the cornea is described in U.S. Pat. Nos. 4,326,529 to Doss et al. and 4,381,007 to Doss. These patents describe the non-invasive introduction of RF probes onto the cornea. The RF generating source is placed on the anterior surface of the cornea and saline solution is used to cool the corneal surface as the radio frequency current enters the eye. The RF apparently heats various stroma within the cornea and thereby reshapes the corneal surface.

Laser treatment of the corneal surface has been well described. Lasers have been used both to reshape the surface of the cornea and to remove tissue from the surface of the cornea. U.S. Pat. No. 5,263,951 to Spears et al. is directed to laser treatment of the cornea for correcting nearsightedness, farsightedness and astigmatism. The corneal stroma is heated with laser energy. A permanent change to the shape of the cornea results without incising, coagulating, scarring or ablating the stroma. A $Co:MgF_2$ solid-state laser is pumped by a continuous wave Nd:YAG laser to produce a continuous average output of from 0.5 to 2.0 watts at a wavelength of from 1.55 to 2.25 microns. The controlled laser energy is delivered to the cornea by an optical fiber that connects to a probe assembly that is held in fixed relation to the cornea. The inventors note a variety of lasers that will provide wavelengths in the range of about 1.38 microns to about 2.70 microns and with the desired absorption coefficient in water (between 5 $cm^{-1}$ to 114 $cm^{-1}$). These lasers can be constructed using $Holmium^{+3}$ ions, $Thulium^{+3}$ ions or $Erbium^{+3}$ ions or mixtures thereof in either a YAG (yttrium-aluminum-garnet), YSGG (yttrium-silicon-gadnolinium-garnet) or YLF (yttrium-lanthanum-fluoride) crystalline media.

U.S. Pat. No. 5,281,211 to Parel et al. involves the use of a laser energy source for marking a cornea in transplanting surgery or keratoplasty, in incising or excising tissue for radial or curved keratotomy or in thermokeratoplasty. A laser source that generates pulsed laser beams is used for ablation of anterior portions of the cornea. These lasers are noted to include those that emit infrared pulses having wavelengths of 2000 to 3000 nm such as Hydrogen Fluoride (HF) lasers and Erbium-YAG lasers. Lasers that emit ultraviolet pulses having wavelengths of less than 200 nm such as Argon Fluoride lasers are also useful. Where desirable to heat corneal tissue without ablation, the laser sources selected are those that emit in the 1300 to 3300 nm wavelength range, such as C.W. HF or Holmium or Nd:YAG lasers. The patent further describes the projection of the laser beams onto the cornea for incisions or excisions for keratotomy, for transplanting surgery and for curing refractive errors by thermokeratoplasty.

U.S. Pat. No. 5,219,344 to Yoder, Jr. et al. further describes the use of laser radiation to ablate corneal, tissue. The cooperative use of an indexable mask, zoom-lens system and laser-beam attenuator is said to produce the desired optical-curvature corrections or reproduce the original corneal curvature for the acceptance of a corneal transplant, the removal of scar tissue or other anterior surface damage to the cornea. The laser selected emits at a tissue-ablating wavelength which may be in the infrared 2900 nm region but is preferably in the ultraviolet 190 nm region such as the radiation emitted from an argon fluoride laser. Other sources are noted to include various gas lasers that operate at tissue ablating ultraviolet wavelengths and crystal lasers where frequency modifying techniques have been applied.

The above noted patents describe the use of laser radiation for ablation of anterior surface corneal tissue. None of these patents suggest the use of laser energy applied beneath the anterior surface of the cornea to desiccate or ablate stromal tissue.

The ablation of tissue in various other regions of the body has been previously studied. U.S. Pat. No. 5,107,513 to Sagie et al. describes the general use of three types of lasers. Carbon dioxide ($CO_2$) laser radiation is intensely absorbed by water and thus acts as a surgical knife and vaporizer, its penetration depth in tissue being 0.03 mm. Argon lasers are minimally absorbed by water but intensely absorbed by hemoglobin and penetrate 1 to 2 mm in most tissue. These lasers are especially useful in coagulating bleeding points in small superficial vessels. Neodymium-Yttrium-Aluminum-Garnet (Nd:YAG) lasers are poorly absorbed by both water and hemoglobin. These lasers are able to penetrate large volumes of tissue, blood clots and coagulate large bleeding vessels. A Holmium laser with a 2100 nm wavelength has good cutting capabilities and its coagulating properties are similar to those of the Nd:YAG laser, penetrating to about 0.4 mm for most tissue. The Holmium laser was noted to be useful for the following applications: (1) in the gastrointestinal tract for bleeding ulcers, excision of lesions, recanalization of obstruction and arresting of massive bleeding; (2) in general surgery for cutting without bleeding; (3) in urology for treatment of the bladder; (4) for creation of vascular anastomoses; (5) for aneurysms, patent ducts, varicose veins and hemangiomas to generate thrombosis; (6) for dissolution of gall bladder stones by insertion of a fiber optic into the bile duct; (7) for destruction of tumors in the bronchial tree; (8) in gynecology for fallopian tube shrinkage and removal of polyps, benign tumors and septum and for ablation of the endometrium for menorrhagia; (9) in cardiac surgery for treatment of obstructed valves; and (10) in neurosurgery for removal of solid as well as vascular tumors.

U.S. Pat. No. 5,147,354 describes the use of a mid-infrared laser endoscope for performing arthroscopy. Holmium:YAG and Holmium:YLF lasers with wavelengths in the 1800 to 2200 nm range are used for producing laser ablations in a fluid field. The radiation is said to be easily transmitted through a conventional quartz optical fiber.

The above-described references note the benefits of using lasers for a number of surgical applications including ophthalmologic surgeries. The references that describe laser surgery of the eye are limited to applications of laser radiation to the anterior surface of the cornea rather than desiccation or ablation of tissue in the stromal area of the cornea.

SUMMARY OF THE INVENTION

This invention is a method of altering the shape of the anterior surface of the cornea using laser radiation applied to the stromal tissue of the cornea. The procedure, in its preferred variations, does not entail significant surgical modification of the anterior corneal surface or of Bowman's layer of the eye, except, in certain situations, adding surface incisions to act either to relieve anterior surface stress or to provide access for the laser energy probe.

A laser probe is a further portion of this invention. It is used to desiccate or ablate portions of the corneal stroma, thereby changing the volume of the mass of the cornea posterior to Bowman's layer. By selectively modifying the volume of this region, small amounts of the cornea may be controllably removed or shrunk and, upon removal of the probe from the cornea, the curvature of the anterior surface of the cornea will have changed and the refractive path of light entering the eye will be altered. As noted above, surface incisions may later be added to permit the anterior of the cornea, in particular Bowman's layer, to conform to the underlying corneal tissue removal (volume change), thereby allowing for change in anterior corneal curvature.

The inventive procedure may be used for the treatment of hyperopia (farsightedness) or myopia (nearsightedness). In this procedure, a small incision or access site is made in the anterior surface of the cornea, which incision extends down through Bowman's layer or through the sclera and into the intrastromal volume of the cornea. A laser probe is introduced through the incision and guided to the target site in the corneal stroma. Activation of the ablation laser will cause vaporization of the region of the cornea adjacent to the tip of the probe. Activating the desiccation laser will shrink or necrose the region of the cornea adjacent to the tip of the probe. After an appropriate necrosis, removal or shrinking of material is accomplished, the probe is removed. The anterior surface of the cornea then relaxes to conform to the collapse or shrinkage of corneal tissue resulting from the laser treatment. In some instances, a modest incision in the anterior surface of the cornea may be desirable to facilitate curvature relaxation of the anterior corneal surface.

Another preferred procedure involves the alleviation of astigmatism. Small partial depth incisions may be made into the anterior surface of the cornea through Bowman's layer or through the sclera adjacent to the cornea to get under Bowman's layer but not reaching so far as the posterior corneal surface or the anterior chamber. The incisions allow for the introduction of the laser probe into the cornea or sclera in order to reach the corneal mass below the anterior surface which must be reduced to produce a symmetric corneal surface. A selected amount of material is removed or desiccated to alleviate the non-regularity of the corneal anterior surface.

BRIEF DESCRIPTION OF THE DRAWINGS

FIGS. 6A to 6B and 7 to 7B show top and side views of inventive circular laser probe tips.

FIGS. 8A to 8B and 9 to 9B show top and side view of inventive straight laser probe tips.

DESCRIPTION OF THE INVENTION

Prior to explaining the details of the inventive procedures and devices, a short explanation of the physiology of the eye is needed.

Figure 1:
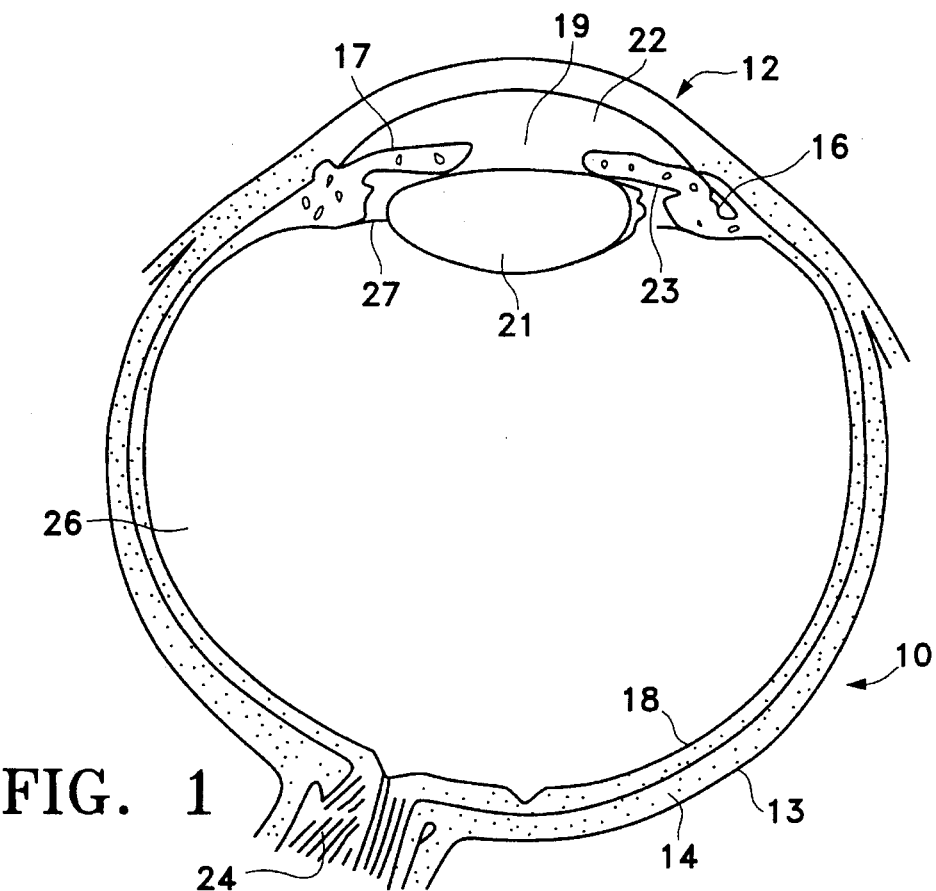
FIG. 1 is a schematic illustration of a horizontal section of the eye.

FIG. 1 shows a horizontal cross-section of the eye with the globe (11) of the eye resembling a sphere with an anterior bulged spherical portion representing the cornea (12).

The globe (11) of the eye consists of three concentric coverings enclosing the various transparent media through which the light must pass before reaching the light-sensitive retina (18). The outermost covering is a fibrous protective portion the posterior five-sixths of which is white and opaque and called the sclera (13), and sometimes referred to as the white of the eye where visible to the front. The anterior one-sixth of this outer layer is the transparent cornea (12).

A middle covering is mainly vascular and nutritive in function and is made up of the choroid, ciliary body (15), and iris (17). The choroid generally functions to maintain the retina (18). The ciliary body (16) is involved in suspending the lens (21) and accommodation of the lens. The iris (17) is the most anterior portion of the middle covering of the eye and is arranged in a frontal plane. It is a thin circular disc similar in function to the diaphragm of a camera, and is perforate near its center by a circular aperture called the pupil (19). The size of the pupil varies to regulate the amount of light which reaches the retina (18). It contracts also to accommodation, which serves to sharpen the focus by diminishing spherical aberration. The iris divides the space between the cornea (12) and the lens (21) into an anterior chamber (22) and the posterior chamber (23). The innermost portion of covering is the retina (18), consisting of nerve elements which form the true receptive portion for visual impressions.

The retina (18) is a part of the brain arising as an outgrowth from the fore-brain, with the optic nerve (24) serving as a fiber tract connecting the retina part of the brain with the fore-brain. A layer of rods and cones, lying just beneath a pigmented epithelium on the anterior wall of the retina serve as visual cells or photoreceptors which transform physical energy (light) into nerve impulses.

The vitreous body (26) is a transparent gelatinous mass which fills the posterior four-fifths of the globe.(11). At its sides it supports the ciliary body (16) and the retina (18). A frontal saucer-shaped depression houses the lens.

The lens (21) of the eye is a transparent bi-convex body of crystalline appearance placed between the iris (17) and vitreous body (26). Its axial diameter varies markedly with accommodation. A ciliary zonule (27), consisting of transparent fibers passing between the ciliary body (16) and lens (21) serves to hold the lens (21) in position and enables the ciliary muscle to act on it.

Referring again to the cornea (12), this outermost fibrous transparent coating resembles a watch glass. Its curvature is somewhat greater than the rest of the globe and is ideally spherical in nature. However, often it is more curved in one meridian than another giving rise to astigmatism. Most of the refraction of the eye takes place through the cornea.

Figure 2:
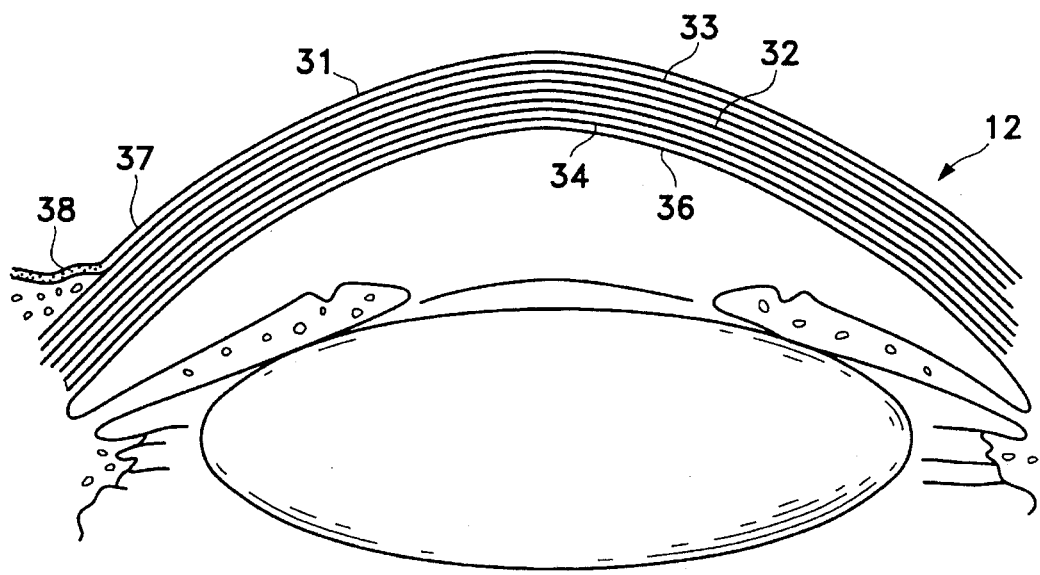
FIG. 2 is a schematic illustration of the anterior portion of the eye, showing various layers of the cornea.

FIG. 2 is a more detailed drawing of the anterior portion of the globe showing the various layers of the cornea (12) making up the epithelium (31).

An anterior limiting lamella (33), referred to as Bowman's membrane or layer, is positioned between the epithelium (31) and the stroma (32) of the cornea. When I refer to the "corneal mass," I mean the various stroma (32) between the Bowman's layer (33) and the Descemet's membrane (34). The corneal stroma (32) are made up of lamellae having bands of fibrils parallel to each other and crossing the whole of the cornea. While most of the fibrous bands are parallel to the surface, some are oblique, especially anteriorly. A posterior limiting lamella (34) is referred to as Descemet's membrane. It is a strong membrane sharply defined from the stroma (32) and resistant to pathological processes of the cornea.

The endothelium (36) is the most posterior layer of the cornea and consists of a single layer of cells and function to maintain transparency of the cornea (12). These epithelial cells are rich in glycogen, enzymes and acetylcholine and their activity regulates the transport of water and electrolytes through the lamellae of the cornea (12). The limbus (37) is the transition zone Between the conjunctiva (38) and sclera on the one hand and the cornea (12) on the other.

There are a variety of different lasers which would be suitable in this invention. Lasers that emit radiation at a wavelength less than about 1500 nm will desiccate tissue, that is the tissue will heat up and will necrose with little immediate denaturation or discoloration. This is also referred to as coagulation. Lasers that emit radiation greater than about 1500 nm will ablate the tissue, that is the tissue will vaporize. Where a thin layer of tissue is vaporized, the tissue will appear to have been cut, thus this may be referred to as cutting. Lasers that emit in wavelengths less than 1500 nm (and in the ultraviolet range) include Excimer lasers (200 nm), Argon lasers (400–600 nm), Krypton lasers (700 nm), Dye lasers (200–900 nm) and Nd:YAG lasers (1000 nm). Lasers that emit radiation at or greater than 1500 nm (and in the infrared range) include Ho:YAG and Ho:YLF lasers (1800–2200 nm), Erbium:YAG lasers (2800), Hydrogen fluoride lasers (2900 nm) and $CO_2$ lasers (10,000 nm).

Figure 3:
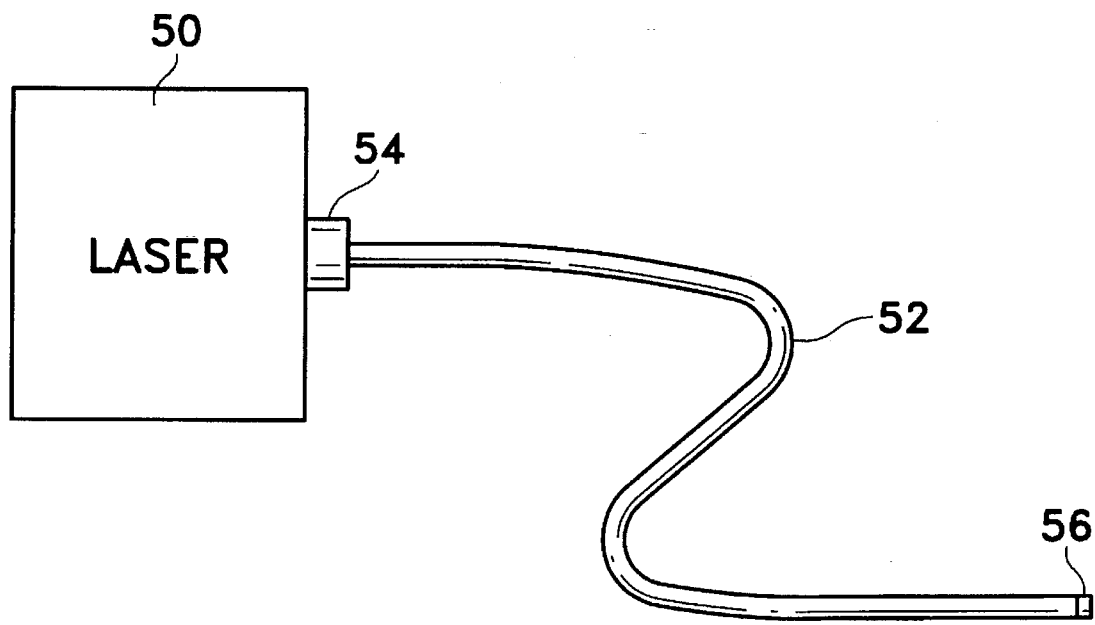
FIG. 3 is a schematic diagram of the device of the invention.

The laser radiation described above is used to cut, ablate, or desiccate tissue in the corneal stroma of a patient's eye. In order to accomplish this, a fiber optic system as schematically shown in FIG. 3 is used. A laser source (50) can be any of the lasers described above. The laser is coupled to the proximal end of a suitable fiber (52) by means of a focusing lens (54) or other similar coupling device. The fiber may be a single 100 micron diameter, low-OH, silica optic or other similar fiber or may be comprise a bundle of fibers of appropriate diameter (of between about 10 and 2000microns). The fiber typically produces no more than a 15% transmission loss over lengths of ten meters. The probe (56) comprises the distal end of the fiber (52) and is inserted into an incision made in the corneal stroma as is described in detail below.

FIGS. 4A through 4D show in schematic fashion, one procedure for treating hyperopia (farsightedness), myopia (nearsightedness), or astigmatism. This schematic procedure shows features which may be common to all of the processes of this invention. Generally, the procedure includes the step of producing one or more incisions, often towards the periphery of the cornea. These incisions penetrate Bowman's layer in the anterior surface of the cornea and extend down into the corneal mass or corneal volume. Alternatively, the probe may be inserted into the corneal volume without penetration of the anterior surface cornea, e.g., by access through a partial depth incision made in the sclera next to the cornea. In any event, if an anterior access partial depth incision is contemplated, an optional step at this point may be the insertion of a lamellar separator to separate the various stroma lamellae within the cornea at the depth of the entry incision. This allows the subsequent step of inserting the laser probe to take place with greater ease. The laser probe is introduced into the stromal lamellar cavity so produced. Depending on the refractive effect desired, the probe is moved inside the intralamellar space previously formed and activated to desiccate or ablate specific geometric regions of the cornea. Desirably, after the completion of the corneal volume ablation or desiccation step, the curvature of the corneal surface is then measured. The procedure may be repeated if insufficient correction has occurred. If needed, Bowman's layer and a small amount of underlying stromal tissue may be lightly cut on the anterior surface adjacent to or above the site of the volume reduction to allow the anterior corneal surface to change.

Returning to the specifics of FIGS. 4A to 4D, FIG. 4A shows an eye (100) having a pupil (102) and a cornea (104).

In the outer radius of cornea (104) are found two small partial depth incisions (106) which have been cut through Bowman's layer into the corneal mass as shown in FIGS. 1 and 2. These incisions may be cut radially or circumferentially and are shown for discussion purposes to be radial.

Figure 4A:
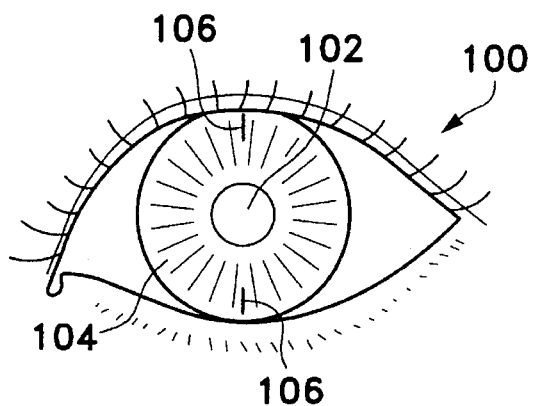
FIGS. 4 to 4E show schematic process for treatment of hyperopia using the procedure of this invention.
Figure 4B:
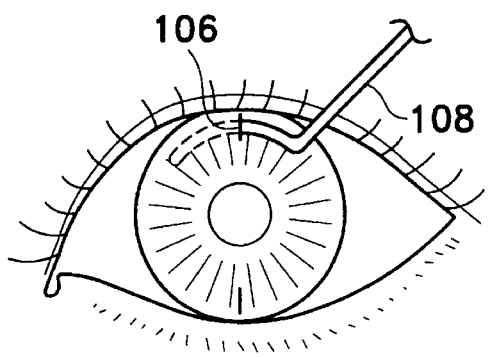

It should be understood, however, that although two access partial depth incisions (106) have been portrayed in FIG. 4A, the number of such access sites (106) is not important. If a semi-circular lamellar separator (108) as shown in FIG. 4B is used, then the number of access sites (106) may be desirably two in number. If lamellar separators of shorter arc segments are used, more numerous slits may be desired. If a nearly circular lamellar separator is used, a single access site (106) may be sufficient.

Figure 4C:
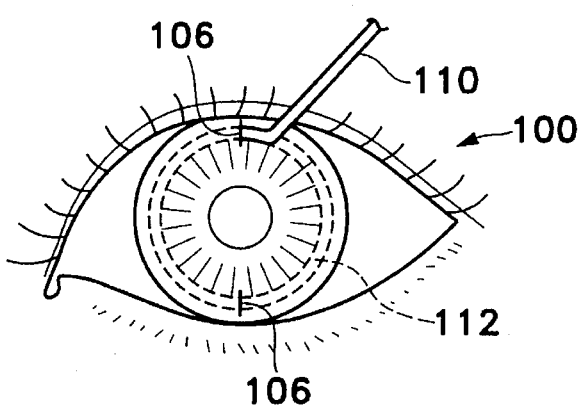

FIG. 4B shows the introduction of the optional dissector blade or lamellar separator (108) to separate the lamella found in the cornea. The separator (108) is rotated until a circular channel is made in the corneal periphery, and is rotated back out of the eye. A similar procedure takes place on the other access site shown in FIG. 4A. FIG. 4C shows the insertion of a laser probe (110) into the route (112) formed in the intrastromal region shown in FIG. 4B. The probe is energized following complete insertion. The laser source is deactivated and the probe is moved to a new site. The probe is again energized. This stop, move and activate system is continued until the desired corneal volume change is obtained, that is until sufficient tissue has been ablated or desiccated to achieve the desired refractive effects.

Figure 4D:
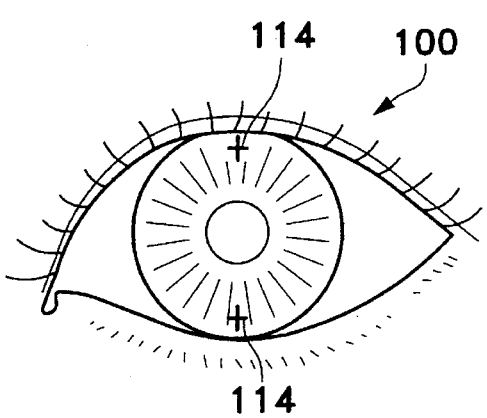
Figure 4E:
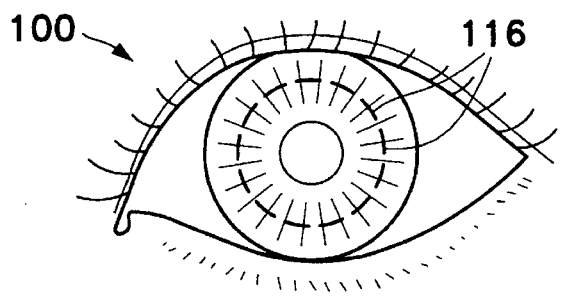

FIG. 4D shows the eye (100) after completion of the ablation procedure. It may be desirable to place a small stitch (114) in any access site (106) in the cornea to ensure healing of the access site and minimize the potential for infection. FIG. 4E shows the eye (100) following relief cuts (116) that may be necessary in some instances to allow the anterior corneal surface to more closely conform to the underlying corneal tissue removal (volume change) thereby allowing for greater change in anterior corneal curvature. These relief cuts may be circumferential as shown or they may be radial depending on the desired refractive effect. Further, the relief cuts may be continuous or may be interrupted as shown. In any case, these cuts will be shallow cuts such that they penetrate Bowman's layer and possibly a portion of the underlying corneal stroma.

The above-description generally indicates the method of the present invention. Specific methods of treatment will be described in the Examples below.

It should be apparent from the description above, that the step of desiccating, necrosing or ablating the tissue from within the corneal mass lessens the volume of that mass in specific regions of the cornea. Consequently, the anterior sections of the cornea will become flatter or steeper and will alleviate the improper previous refraction of light. Some of the possible changes in corneal thickness and their relationship to the radius of curvature of the central corneal surface are described in *Jose Barraquer: Father of Modern Refractive Keratopasty*, in Refractive and Corneal Surgery, Vol. 5, May/June 1989, pages 177–193, which is hereby incorporated by reference in its entirety. This paper describes the so-called "Law of Thickness" which indicates that when corneal volume is reduced in the periphery, central corneal steepening occurs and when a volume of tissue is removed in the center, central corneal flattening occurs. The inventive method and laser systems aim to reduce corneal volume in controlled geometric areas of the corneal stroma to achieve refractive correction.

Figure 5A:
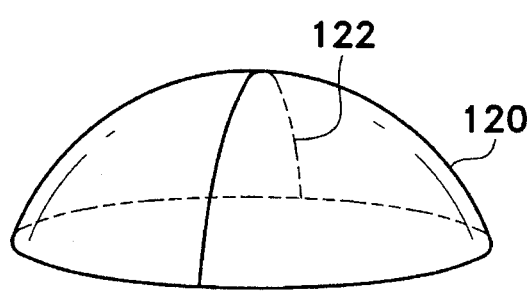
FIGS. 5A to 5D show schematic diagrams of astigmatic and normal eyes.
Figure 5B:
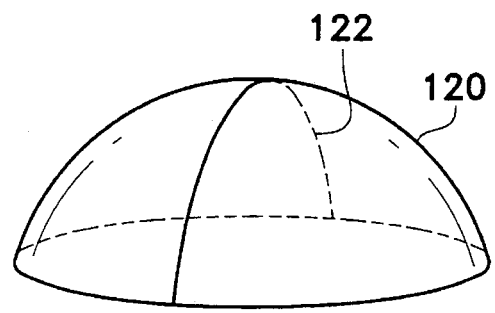
Figure 5C:
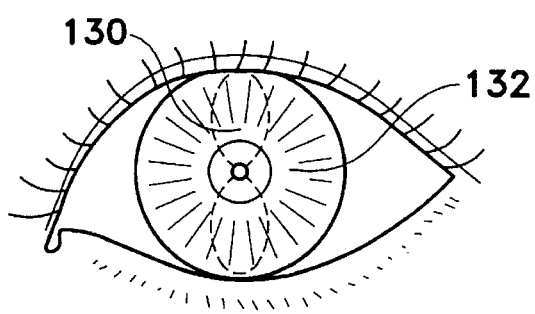
Figure 5D:
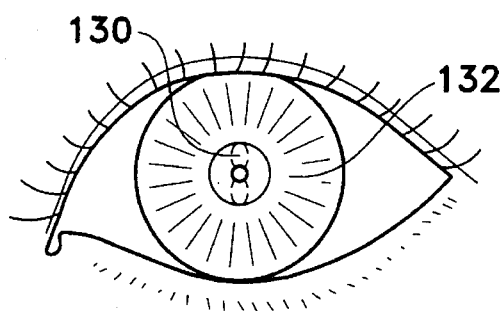

The method and laser systems of the present invention may also be useful in the treatment of astigmatism. Astigmatism occurs, generally, when the curvature of the anterior surface of the cornea is not regular, as one passes about the meridians on the anterior surface of the cornea resulting in a steep and flat axis. FIG. 5A and 5B are schematic perspective views that show an astigmatic and normal eye, respectively. In an astigmatic eye, two axes are generally identified, corresponding to the steepest (120) and flattest (122) axis of curvature. The steepest axis is also known as the axis of astigmatism (120). To correct astigmatism using this invention, one must flatten the curvature of the astigmatic axis such that the cornea becomes reasonably symmetrical and more spherical. FIG. 5B shows a normal eye, that is, one in which the curvature of all axes are the same. FIGS. 5C and 5D show schematic topographical curvature maps of an astigmatic and of a non-astigmatic eye, respectively. In FIG. 5C, region 130 is the steep region whereas region 132 is flatter.

Other configurations of access sites and controlled removal of corneal tissue are apparent. These will be discussed for particular applications in the Examples below. Further, it should be apparent to one appreciating the design of laser systems, that the radiation need not be emitted laterally. Reflective mirrors may be used to refocus the laser and effect tissue located tangentially to the probe. Further, the end of the optical fiber may be shaped to refract the laser radiation. The procedures and devices of the present invention may further be useful in the treatment of more than one indication, for example myopia and astigmatism or hyperopia and astigmatism.

In addition to the laser system shown in FIG. 3, the distal end of the fiber optic 56 may further include a fiber optic probe support. This support may be circular or straight and may vary in its cross-sectional shape. The transmission of radiation from the probe will be axial, that is in the direction of the central axis of the fiber optic at the distal end of the fiber optic. However, the distal end of the fiber optic probe may further include a focusing lens and/or reflecting mirror or combination thereof to allow for transmission of radiation in a direction of between 0° and 180° from axial as defined above.

FIGS. 6–9 A and B show top and side views of circular and straight laser probe supports. The probe support is made of any type of material that is biologically compatible and has sufficient structural integrity to guide the fiber optic through the lamellar channel. Appropriate materials include but are not limited to metals such as stainless steel, titanium, cobalt chrome alloys, polymeric materials such as polyether ether ketone, nylons, acrylics, polyesters, polyurethanes and polyolefins, composite materials and ceramics or combinations thereof. In addition to their use for guiding the fiber optic when the tissue is being desiccating or ablating, these probe supports may be useful as lamellar separators for separating the corneal stroma once the partial depth incisions have been made.

FIGS. 6 and 7 A and B are top and side views of a fiber optic (52) with a circular probe support (200) and (210). The probe supports (200) and (210) coaxially surround the fiber optic (52) and the distal end (56) of the fiber optic (52) is coincident with the distal ends (202) and (212) of the probe supports (200) and (210) respectively.

The transmission of radiation from the probe support shown in FIGS. 6 A and B will be axial as defined above, and further will be coaxial with axis of the lamellar channel.

The transmission of radiation from the probe support, shown in FIGS. 7 A and B will be axial as defined above, and further will be of from between 0° and 90° from coaxial with axis of the lamellar channel. A focusing lens or reflecting mirror or combination thereof (214) may be attached at the distal end (212) of the probe support (210) to allow for reflection of radiation of from between about 0 to 180° from axial.

FIGS. 8 and 9 A and B are top and side views of a fiber optic (52) with straight probe supports (220) and (230). The probe supports (220) and (230) support the fiber optic (52) and the distal end (56) of the fiber optic (52) is coincidental with the distal ends (222) and (232) of the probe supports (220) and (230).

The transmission of radiation from the probe support shown in FIGS. 8 A and B will be axial as defined above, and further will be coaxial with axis of the lamellar channel.

The transmission of radiation from the probe support shown in FIGS. 9 A and B will be axial as defined above. In addition, a focusing lens or reflecting mirror or combination thereof (234) may be attached at the distal end (232) of the probe support (230) to allow for reflection of radiation of from between about 0° to 180° from axial, and shown as 90°.

The following Examples are intended to describe particular embodiments of the invention but are in no way intended to limit the invention in any manner.

EXAMPLES

Example 1—The Correction of Astigmatism

Figure 10A:
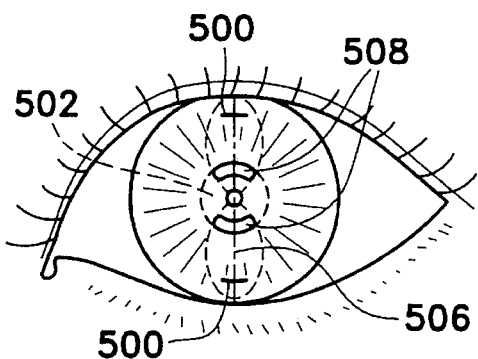
FIGS. 10A to 10G are schematic diagrams showing top views of eyes wherein various laser surgeries for altering corneal curvature have been carried out.
Figure 10B:
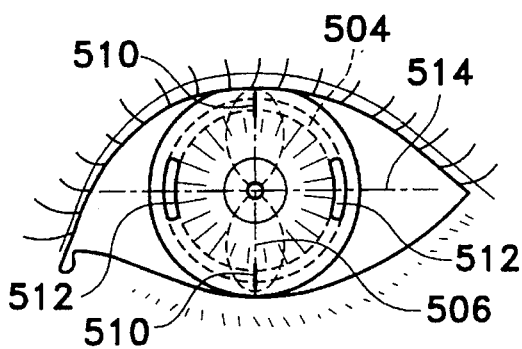

In order to correct the astigmatic eye shown in FIGS. 5A and 5C such that it becomes more similar to that shown in FIGS. 5B and 5D, a process similar to that describe above with regard to FIGS. 4A–4D is carried out. As shown in FIGS. 10A and 10B, radial or circumferential partial depth incisions (500) are made in the periphery of the cornea. A lamellar separator is inserted to create zones of separated lamellae (502) and (504) for the insertion of the laser probe.

Two different approaches are possible to correct the astigmatic eye. In the first approach shown in FIG. 10A, a radial zone (502) of separated lamellae will be formed beneath the astigmatic axis (506). Following separation of the lamellar tissue, the laser probe, with or without a probe support such as one of those shown in FIGS. 8 and 9 A and B, is inserted through the partial depth incision (500). The probe is then activated to change the paracentral corneal volume (508), that is the volume near the center of the cornea, by ablation of the tissue under the figure—8—shaped astigmatic axis (506). The probe may be moved inside the zone of separated lamellae (502) or may be removed and inserted into a second partial depth incision (500) for ablation (or desiccation) of another section of paracentral corneal volume (508). Once ablation is completed, the probe is withdrawn. Relief cuts on the anterior cornea may be necessary as described above to allow the surface of the cornea to conform to the underlying tissue removal. In this way, the steep astigmatic axis is flattened such that the cornea becomes reasonably symmetrical and spherical.

A second approach to the treatment of an astigmatic eye is to steepen the flat astigmatic axis as shown in FIG. 10B. In this approach, the lamellar separation zone will be formed in the periphery of the cornea (504). Two or more partial depth incisions (510) are placed in the corneal periphery, beneath the astigmatic axis. Following separation of the lamellar tissue, the laser probe, with or without a probe support such as one shown in FIGS. 6 and 7 A and B, is inserted sequentially through each partial depth incision.

The probe is then activated, deactivated, moved to a second position to be ablated or desiccated and the process is repeated to change the volume of the tissue (512) in the lamellar separation zone (504). The probe is then withdrawn and inserted into a second partial depth incision and the process repeated. This insertion, activation, deactivation, removal and reinsertion system is repeated to change the volume of corneal tissue under the flat axis (514) as shown in FIG. 10B. Once the probe is withdrawn from the last partial depth incision, relief cuts may be made to allow the surface of the cornea to conform to the underlying tissue modification. In this way, the flat axis (514) is steepened such that the cornea becomes reasonably symmetrical and spherical.

Example 2—The Correction of Hyperopia

Figure 10C:
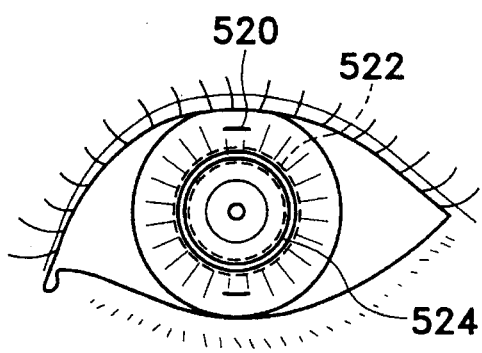
Figure 10D:
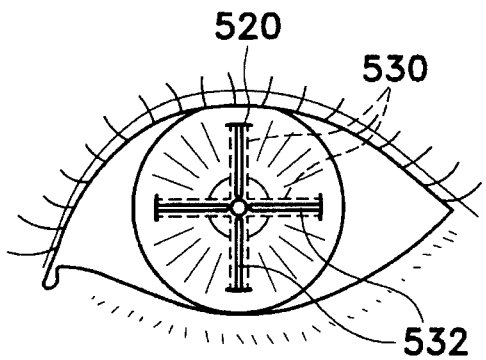
Figure 10E:
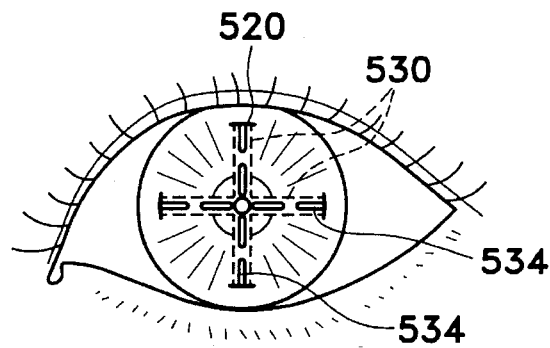

In order to correct the hyperopic eye, a process similar to that described with regard to FIGS. 4A–4D is carried out. As shown in FIGS. 10C, 10D, and 10E, radial or circumferential partial depth incisions, in this case shown to be circumferential incisions (520) are made in the periphery of the cornea. A lamellar separator is inserted to create a lamellar pathway (522) or (530) for the insertion of the laser probe.

Two different approaches are possible to correct the hyperopic eye. In the first approach shown in FIG. 10C, partial depth incisions (520) are made in the peripheral cornea and a circumferential lamellar separation zone (522) will be formed beneath the corneal surface. Following separation of the lamellar tissue, the laser probe (by itself or with a circular probe support as shown in FIGS. 6 and 7 A and B) is inserted through the partial depth incision (520). The probe is then activated to change the corneal volume (524), by ablation or desiccation of the tissue (524) in the channel (522). Once ablation is completed, the probe is withdrawn. Relief cuts on the anterior cornea may be necessary as described above to allow the surface of the cornea to conform to the underlying tissue removal. In this way, the central corneal surface is steepened such that the corneal curvature is improved.

A second approach to the treatment of a hyperopic eye is to make two or more partial depth incisions in the periphery of the cornea. In this approach shown in FIGS. 10D and 10E, the two or more radial lamellar Separation zones will be formed in the periphery of the cornea (530). Following separation of the lamellar tissue, the laser probe (by itself or with a straight probe support as shown in FIGS. 8 and 9 A and B) is inserted sequentially through the partial depth incisions. The probe is then activated, deactivated, moved to a second position to be ablated or desiccate and the process is repeated to change the volume of the tissue (532) and (534) near the partial depth incision. The probe is then withdrawn and inserted into a second partial depth incision and the process repeated. This insertion, activation, deactivation, removal and reinsertion system is repeated to change the volume of corneal tissue as shown in FIGS. 10D and 10E. In this way the tissue desiccated or ablated can either form a continuous path (532) or can be interrupted points along the radial lamellar separation channel (534). Once the probe is withdrawn from the last partial depth incision, relief cuts may be made to allow the surface of the cornea to conform to the underlying tissue modification. In this way, the flat corneal surface is steepened centrally such that the corneal curvature is improved.

Example 3—The Correction of Myopia

Figure 10F:
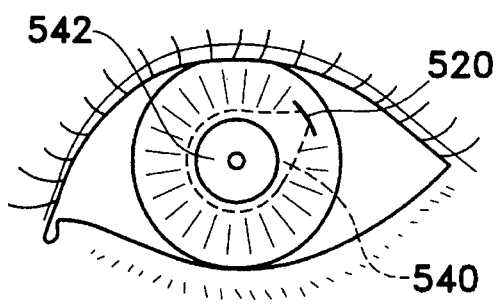
Figure 10G:
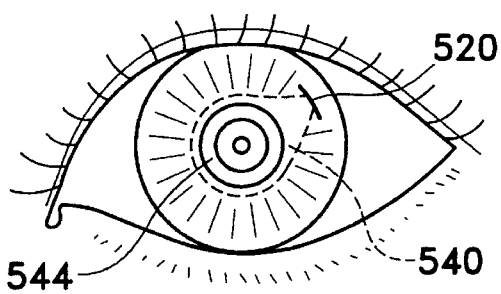

In order to correct myopia, a process similar to that described with regard to FIGS. 4A–4D is carried out. As shown in FIGS. 10F and 10G, one or more partial depth incisions (520) are made in the peripheral cornea and a radial lamellar separation zone (540) will be formed beneath the corneal surface. Following separation of the lamellar tissue, the laser probe (by itself or using one of the straight or circular probe supports as shown in FIGS. 6 to 9 A and B) is inserted through the partial depth incision (520). The probe is then activated to change the corneal volume by ablation or desiccation of a disc shaped volume of tissue (542) or a washer shaped volume of tissue (544) in the channel. Once ablation is completed, the probe is withdrawn. Relief cuts on the anterior cornea may be necessary as described above to allow the surface of the cornea to conform to the underlying tissue removal. In this way, the central corneal surface is steepened such that the corneal curvature is improved.

The foregoing examples of procedures and devices according to the present invention are only representative and are not meant to be limiting in any manner. Other embodiments, areas of application, methods of use of the present invention, within the scope of the claims appended hereto will be evident to those skilled in this art. Other embodiments of the procedures and devices without the scope of the claims but within the spirit of the invention described herein are considered to be equivalent to those procedures and devices claimed.

We claim:

1. A procedure for altering the shape of the anterior corneal surface of an eye having a corneal mass posterior to the anterior corneal surface, comprising the steps of:

producing at least one access site into the corneal mass posterior to Bowman's layer wherein at least a portion of said access site passes through a portion of the eye outside the corneal mass posterior to Bowman's layer;

introducing through said at least one access site a laser probe; and actuating said laser probe to modify the volume of the corneal mass adjacent to said probe.

2. The procedure of claim 1 wherein the step of modifying the corneal mass is by ablation.

3. The procedure of claim 1 wherein the step of modifying the corneal mass is by desiccation.

4. The procedure of claim 2 wherein the laser emits radiation at a wavelength of greater than about 1500 nm.

5. The procedure of claim 4 wherein the laser is selected from the group consisting of Holmium:YAG, Holmium:YLF, Erbium:YAG, Hydrogen Fluoride and $CO_2$ lasers or mixtures thereof.

6. The procedure of claim 3 wherein the laser emits radiation at a wavelength of less than about 1500nm.

7. The procedure of claim 6 wherein the laser is selected from the group consisting of Excimer, Argon, Krypton, Neodymium: YAG and Dye lasers or mixtures thereof.

8. The procedure of claim 1 wherein the modification of the volume of the corneal mass is to correct myopia.

9. The procedure of claim 1 wherein the modification of the volume of the corneal mass is to correct hyperopia.

10. The procedure of claim 1 wherein the modification of the volume of the corneal mass is to correct astigmatism.

11. The procedure of claim 1 additionally comprising providing a relief cut in at least a portion of Bowman's layer.

12. The procedure of claim 1 wherein said at least one access site passes through the anterior corneal surface.

13. The procedure of claim 1 wherein said at least one access site passes through a portion of the sclera adjacent to the cornea.

* * * * *

UNITED STATES PATENT AND TRADEMARK OFFICE
CERTIFICATE OF CORRECTION

PATENT NO. : 5,599,341

DATED : Feb. 4, 1997

INVENTOR(S) : Mark L. Mathis and Thomas A. Silvestrini.

It is certified that error appears in the above-identified patent and that said Letters Patent is hereby corrected as shown below:

Column 1
 line 34 after "distance" insert -- in --

Column 2
 line 41 delete [C.W. HF] and insert -- C.W.HF --
 line 47 after "corneal" delete [,]

Column 4
 line 40 after "$_4$" insert -- A --

Column 5 line 30 after "globe" delete [.] and insert -- # (a space) --

Column 6
 line 2 delete [Between] and insert -- between -- line 20 after "$CO_2$" insert -- # (a space -- line 31 after "2000" insert -- # (a space) --

Column 7 line 56 delete [*Keratopasty*] and insert -- *Keratoplasty* --

UNITED STATES PATENT AND TRADEMARK OFFICE
CERTIFICATE OF CORRECTION

PATENT NO. : 5,599,341
DATED : Feb. 4, 1997
INVENTOR(S) : Mark L. Mathis and Thomas A. Silvestrini.

It is certified that error appears in the above-identified patent and that said Letters Patent is hereby corrected as shown below:

Column 8
    line 2 after "regular" delete [,]

line 39 after "0°" insert -- # (a space) -- line 65 after "support" delete [,]
    line 67 after "0°" insert -- # (a space) --

Column 9
    line 4 delete [0] and insert -- 0° -- line 46 remove bold from "8"

Column 10
    line 43 delete [Separation" and insert -- separation --

Column 12
    line 16 delete [1500nm] and insert -- 1500 nm --
    line 19 delete [Neodymium: YAG] and insert -- Neodymium:YAG --

Signed and Sealed this

Third Day of October, 2000

Attest:

Q. TODD DICKINSON

*Attesting Officer*      *Director of Patents and Trademarks*